(12) United States Patent
Tsai

(10) Patent No.: US 7,419,467 B2
(45) Date of Patent: *Sep. 2, 2008

(54) MEDICAL INSPECTION DEVICE

(75) Inventor: Jory Tsai, Hudson, MA (US)

(73) Assignee: M³ Electronics, Inc., Hudson, MA (US)

( * ) Notice: Subject to any disclaimer, the term of this patent is extended or adjusted under 35 U.S.C. 154(b) by 594 days.

This patent is subject to a terminal disclaimer.

(21) Appl. No.: 10/938,099

(22) Filed: Sep. 10, 2004

(65) Prior Publication Data

US 2005/0043588 A1    Feb. 24, 2005

Related U.S. Application Data

(63) Continuation-in-part of application No. 10/638,565, filed on Aug. 11, 2003, now Pat. No. 7,137,948, which is a continuation-in-part of application No. 09/683,253, filed on Dec. 5, 2001, now Pat. No. 6,626,825, which is a continuation-in-part of application No. 09/409,127, filed on Sep. 30, 1999, now Pat. No. 6,361,489, which is a continuation-in-part of application No. 09/199,963, filed on Nov. 25, 1998, now Pat. No. 6,186,944.

(51) Int. Cl.
*A61B 1/227* (2006.01)
*A61B 1/04* (2006.01)

(52) U.S. Cl. .................. 600/109; 600/200; 600/130; 600/167; 600/179; 600/118

(58) Field of Classification Search .............. 600/109, 600/129–131, 167, 179, 118, 199, 200; 348/65, 348/66; 433/29
See application file for complete search history.

(56) References Cited

U.S. PATENT DOCUMENTS 4,604,992 A    8/1986  Sato (Continued)

FOREIGN PATENT DOCUMENTS

EP    0140972    4/1983

(Continued)

OTHER PUBLICATIONS

Website: http://www.rfsystem.co.jp/rinfo.html, printed Jul. 30, 2001 (1 sheet).

(Continued)

*Primary Examiner*—John P. Leubecker
(74) *Attorney, Agent, or Firm*—Sampson & Associates, P.C.

(57) ABSTRACT

A dental/medical instrument is provided for use in diagnostic and related patient inspection/examination. The device includes a body having an integral speculum with a video image capture device, a power supply and a display. These components, and user actuatable controls, are integral with the body. The body is adapted for convenient engagement and manipulation by a user's hand to provide a unitary, hand-held device capable of illuminating and capturing an image of a patient, and displaying the image. An autofocus device moves an image sensor relative to a fixed lens array. Components of the image capture device, such as a lens and light emitter, are disposed on a nose portion of the speculum, which is modularly replaceable with alternate nose portions sized and shaped to facilitate various discrete medical/dental examination procedures. Embodiments also includes a tube and controller configured to apply material, capture data, and/or effect movement of the speculum.

33 Claims, 11 Drawing Sheets

U.S. PATENT DOCUMENTS

| | | | |
|---|---|---|---|
| 4,633,304 A | 12/1986 | Nagasaki | |
| 4,742,819 A | 5/1988 | George | |
| 4,884,133 A | 11/1989 | Kanno et al. | |
| 5,142,357 A | 8/1992 | Lipton | |
| 5,227,890 A | 7/1993 | Dowski, Jr. | |
| 5,363,838 A | 11/1994 | George | |
| 5,373,317 A | 12/1994 | Salvati et al. | |
| 5,527,261 A | 6/1996 | Monroe et al. | |
| 5,634,790 A | 6/1997 | Pathmanabhan et al. | |
| 5,658,235 A | 8/1997 | Priest et al. | |
| 5,701,155 A | 12/1997 | Wood et al. | |
| 5,701,904 A | 12/1997 | Simmons et al. | |
| 5,702,345 A | 12/1997 | Wood et al. | |
| 5,733,029 A | 3/1998 | Monroe | |
| 5,751,341 A | 5/1998 | Chaleki et al. | |
| 5,762,605 A | 6/1998 | Cane et al. | |
| 5,873,814 A | 2/1999 | Adair | |
| 5,879,289 A | 3/1999 | Yarush et al. | |
| 5,885,214 A | 3/1999 | Monroe et al. | |
| 5,895,350 A * | 4/1999 | Hori | 600/167 |
| 5,919,130 A | 7/1999 | Monroe et al. | |
| 6,106,457 A | 8/2000 | Perkins et al. | |
| 6,186,944 B1 | 2/2001 | Tsai | |
| 6,252,626 B1 | 6/2001 | Buckley et al. | |
| 6,361,489 B1 | 3/2002 | Tsai | |
| 6,476,979 B1 | 11/2002 | Schaack | |
| 6,485,413 B1 | 11/2002 | Boppart et al. | |
| 6,867,864 B2 * | 3/2005 | Overbeck et al. | 356/402 |

FOREIGN PATENT DOCUMENTS

| | | |
|---|---|---|
| WO | WO-93/15648 A1 | 8/1993 |
| WO | WO-97/15144 A1 | 4/1997 |
| WO | WO-98/02085 A2 | 1/1998 |
| WO | WO-99/42030 A1 | 8/1999 |
| WO | WO-00/30526 A1 | 6/2000 |

OTHER PUBLICATIONS

Website: http://www.rsystem.co.jp/kjibissm21.html, printed Jul. 30, 2001 (3 sheets).

* cited by examiner

MEDICAL INSPECTION DEVICE

This application is a Continuation-In-Part of U.S. patent application Ser. No. 10/638,565, now U.S. Pat. No. 7,137,948 filed on Aug. 11, 2003, entitled "Medical Inspection Device", which is a Continuation-In-Part of U.S. patent application Ser. No. 09/683,253, now U.S. Pat. No. 6,626,825 filed on Dec. 5, 2001, entitled "Medical Inspection Device", which is a Continuation-In-Part of U.S. patent application Ser. No. 09/409,127, now U.S. Pat. No. 6,361,189, filed on Sep. 30, 1999, entitled "Medical Inspection Device", which is a Continuation-In-Part of U.S. patent application Ser. No. 09/199,963, now U.S. Pat. No. 6,186,944, filed on Nov. 25, 1998, entitled "Medical Inspection Device".

BACKGROUND OF THE INVENTION

1. Field of the Invention

The present invention relates to medical and dental optical diagnostic instruments, and more particularly to an integrated hand held viewing scope and display for use as an otoscope, ophthalmoscope, larynx illumination, nasopharynx illuminator, dermatologic magnifier and anoscope.

2. Background Information

Various hand held instruments for use by a physician or dentist during examination of a patient have been known in the art for many years. Such hand held instruments include the otoscope for examination of the ear, ophthalmoscope for examination of the eye, larynx illuminator (throat), nasal pharynx illuminator (nasal passages), dermatologic magnifier (skin) and anoscope (lower G.I. tract).

Also, in the prior art, it has been known to employ miniature or micro-video cameras in connection with various surgical procedures which occur in the operating room. Examples of such video cameras are known as remote head color CCD cameras. These cameras typically employ an array of semi conductive chips using a technology known as charge coupled diode sensors. Such micro-cameras are capable of yielding more than 500 lines of resolution per axis, resulting from the use of 400,000 or more pixels. Use of such micro-video cameras and related equipment, such as endocouplers, have been known for some time in connection with certain types of surgery and, particularly, surgery conducted through the use of small incisions in the body wall in videoendoscopy procedures. Such procedures have become increasingly commonplace in connection with procedures upon the gall bladder, appendix, intestine, etc., where the problem is of an internal nature.

In addition to relatively widespread use of such micro-video technology in the operating room, which includes the display of a procedure upon separate monitors, this technology has also been utilized in the dentist's or physician's office in the context of otherwise routine examination and diagnosis. An example of an instrument incorporating this technology is shown, for example, in U.S. Pat. No. 5,762,605, issued to Cane et al. This device discloses a hand held optical diagnostic instrument including a CCD sensor and an external light source. The instrument is coupled to a discreet monitor which may permit both patient and physician to observe an image of the examination. Moreover, devices of this type may be utilized to produce a video record of such an examination and/or provide either a video tape of the examination or selected print frames thereof.

Such devices may also be used to provide a video link to a satellite or other communications means from a video interface of the system. This may enable consultants to be utilized either in real time, or in a batch mode, to provide "second opinions" to the examining medical personnel or paramedic who may be located in a geographically remote region and/or may possess limited skills in the specialty to which the examination relates. Such activity has become known as telemedicine.

A disadvantage of such devices, however, is that they tend to be awkward to use, as such instruments tend to be difficult for the examining physician to hold, to manipulate and to obtain the necessary views for the examination while simultaneously viewing the image on the remote monitor. This is due to the need for the examining care provider to manipulate the instrument relative to the patient, while looking away from the patient to the monitor. Thus, while many prior art instruments may be designed to facilitate manipulation by the user, the ergonomics of such devices tends to divert the user's attention away from the patient during examination, which may result in discomfort to the patient due to errant manipulation of the instrument. This drawback may be particularly problematic with respect to new users, or those with minimal training in the use of such instruments.

Thus, a need exists for an ergonomically improved hand-held dental/medical instrument which enables a user to simultaneously observe both the patient and the instrument while viewing an image captured thereby.

SUMMARY OF THE INVENTION

According to the present invention, a portable unitary hand-held dental/medical instrument of the type selected from the group consisting of otoscopes, ophthalmoscopes, larynx scopes, nasopharynx scopes, dermatologic scopes, anoscopes, or veterinary scopes is provided. The instrument includes a body having a pistol-grip adapted for engagement by a user's hand. The body includes a frusto-conical speculum disposed thereon, the speculum having a nose with a distal end disposed along an axis of examination, the speculum being sized and shaped to allow location of the distal end a predetermined distance from a target. The instrument further includes at least one lens immovably disposed in the speculum, and at least one light outlet disposed in said speculum. An image sensor is disposed to capture a target image viewed through the lens. An autofocus module is coupled to the image sensor, to move the image sensor relative to the lens. A video display is housed within the body, a wireless communication module is disposed within the instrument, and a voice recognition module is disposed within the instrument. A controller disposed within the instrument, a tube extends from the controller to the distal end of the speculum, and the tube is configured to communicably couple the controller to an exterior of the speculum at the distal end.

Another aspect of the invention includes a method of examining a patient. The method includes utilizing a portable hand-held instrument of the type selected from the group consisting of otoscopes, ophthalmoscopes, larynx scopes, nasopharynx scopes, dermatologic scopes, anoscopes, or veterinary scopes, the instrument including: a body having a pistol-grip adapted for engagement by a user's hand, the body including a speculum disposed thereon; at least one lens immovably disposed in the speculum; at least one light outlet disposed in the speculum; an image sensor disposed to capture a target image viewed through the lens; and an autofocus module coupled to the image sensor, the autofocus module configured to move the image sensor relative to the lens. The instrument also includes a substantially planar video display housed within the body, the video display being disposed within an axis of examination; a wireless communication module disposed within the instrument, configured to communicate with a remote device; and a voice recognition module disposed within the instrument, configured to operate the instrument in response to voice commands. The instrument also includes a controller disposed within the instrument; and a tube extending from the controller to the distal end of the speculum. The method also includes manipulating the instrument relative to a patient while the user simultaneously faces both the patient and the video display.

A still further aspect of the invention includes a portable hand-held instrument of the type selected from the group consisting of otoscopes, ophthalmoscopes, larynx scopes, nasopharynx scopes, dermatologic scopes, anoscopes, or veterinary scopes. This instrument includes a body having a pistol-grip adapted for engagement by a user's hand, the body including a speculum disposed thereon. The speculum has a distal end disposed along an axis of examination, and is sized and shaped to allow location of the distal end a predetermined distance from a target. A fixed lens array and a light outlet are disposed integrally within the body. The fixed lens array includes a filter and a plurality of lenses disposed in spaced relation along the axis of examination. An image sensor is disposed in the body to capture a target image viewed through said lens. An autofocus module is coupled to the image sensor, and is configured to move the image sensor relative to the lens, so that the movement is confined to the body. A video display is disposed within the body, within the axis of examination.

DETAILED DESCRIPTION

Figure 1:
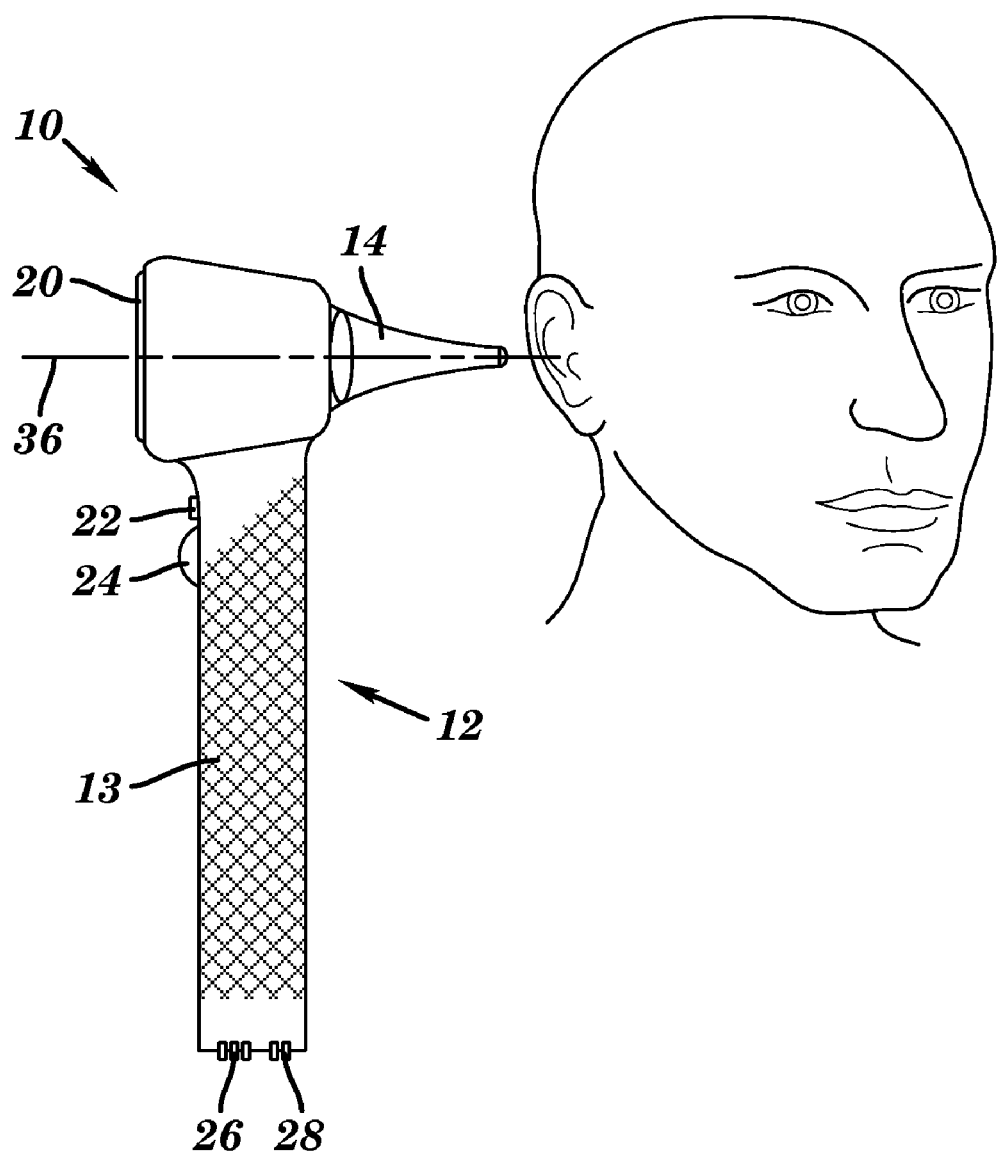
FIG. 1 is a partially perspective elevational view of a dental/medical instrument of the present invention in use relative to a patient.
Figure 2:
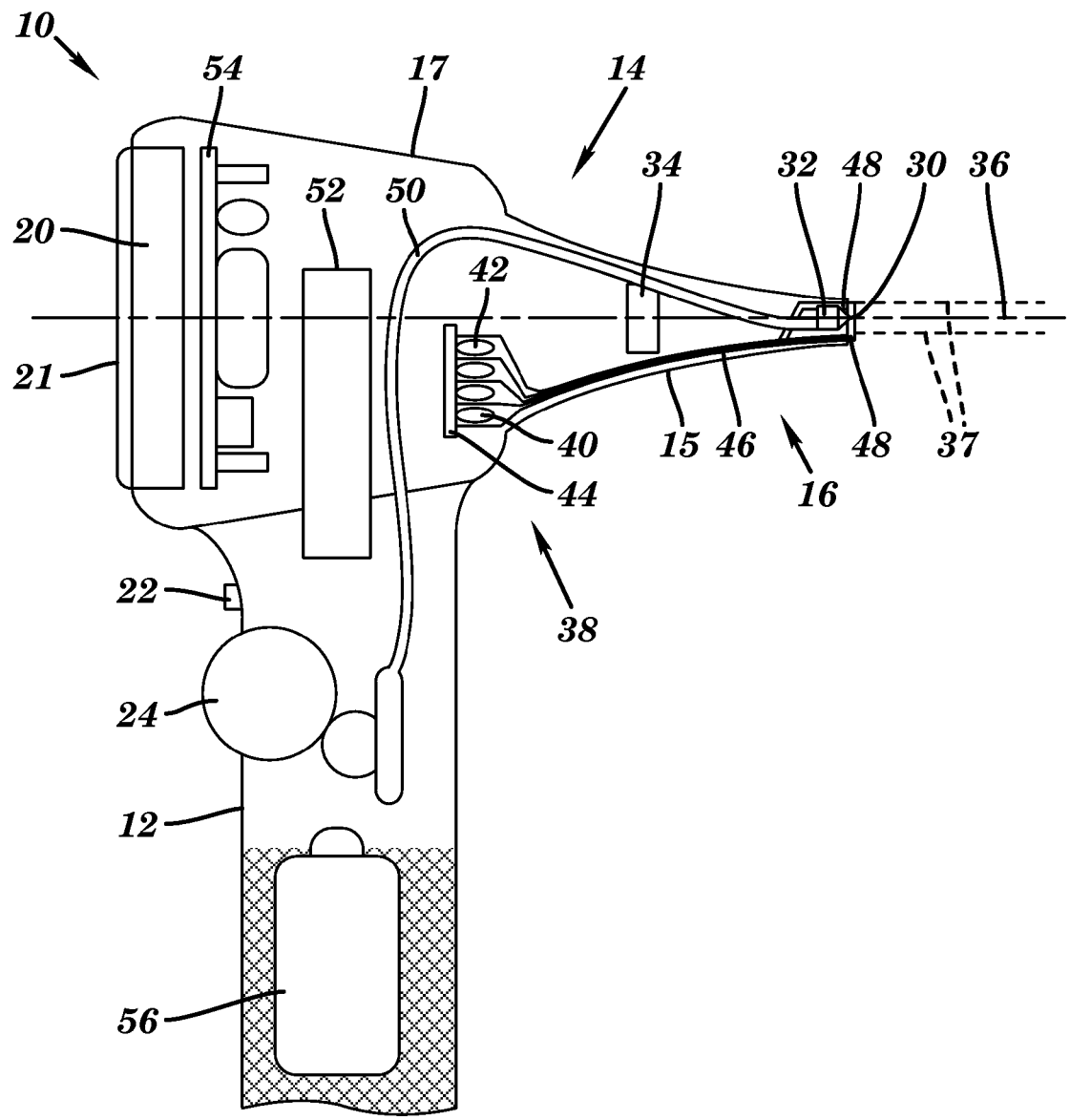
FIG. 2 is an enlarged, broken-away elevational view of a portion of the instrument of FIG. 1.
Figure 3:
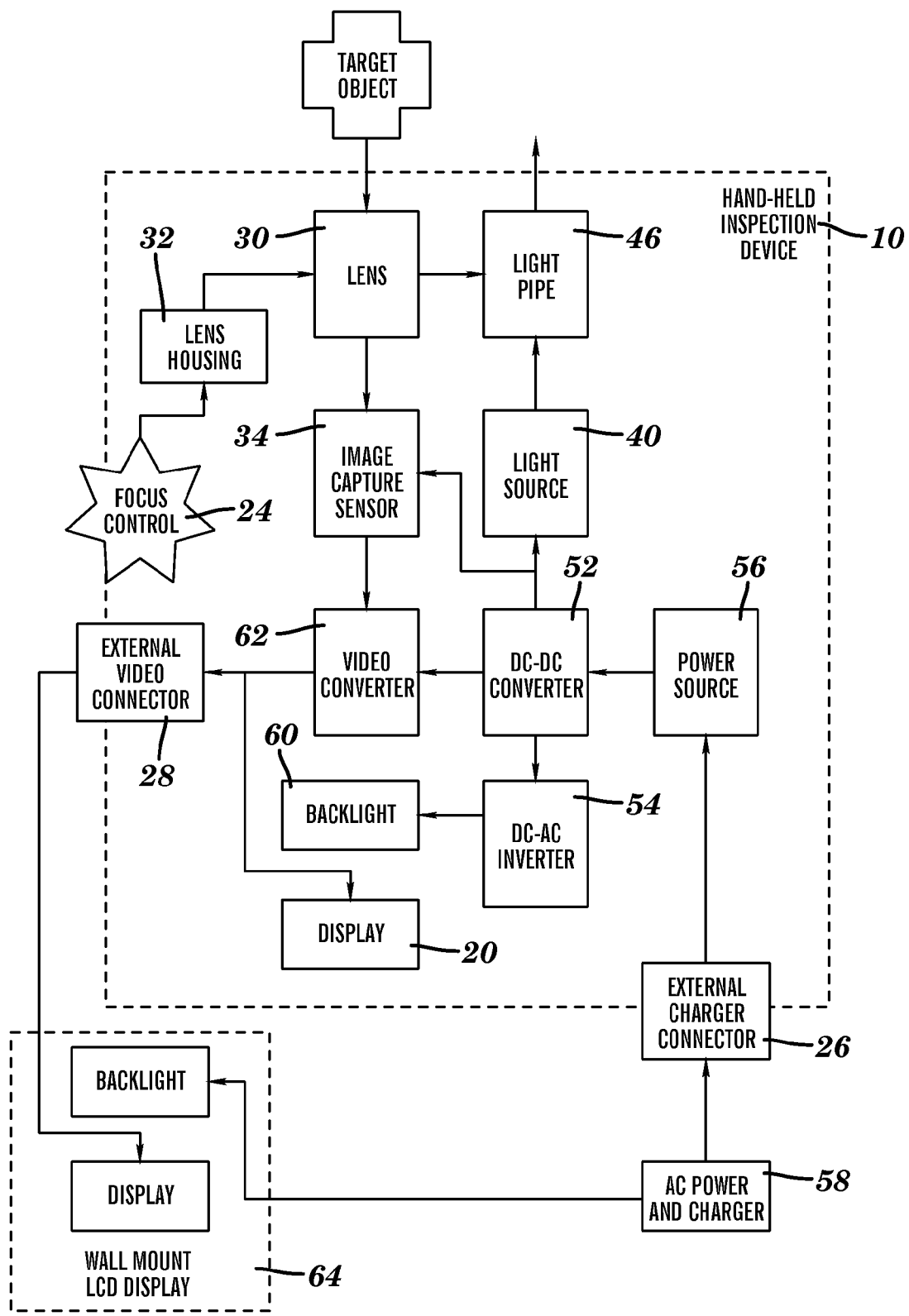
FIG. 3 is a block diagram of the componentry of the present invention.

As shown in FIGS. 1-3, the present invention includes a dental/medical instrument 10 for use in diagnostic and related patient inspection/examination. The device includes a body 12 including an integral speculum 14 with a video image capture device or camera 16, a power supply and a video display 20. These components, in addition to user actuatable controls including a power switch 22 and image focus control 24, are preferably disposed integrally with the body 12. (Portions of the image capture device, such as image sensor 34, as will be discussed hereinbelow, may be disposed remotely from the body 12, and coupled thereto through a port 28.) The body 12 is adapted for convenient engagement and manipulation by a user's hand. The video display is disposed on a display portion of the speculum, while components of the image capture device, such as a lens and light emitter, are disposed on a nose portion of the speculum. As shown in FIGS. 6a-6e, the nose portion is modularly replaceable with alternate nose portions sized and shaped to facilitate various discrete medical/dental examination procedures. The present invention thus provides a unitary, hand-held device capable of illuminating and capturing an image of a patient, and displaying the image.

As used herein, the term "light" is defined as electromagnetic energy within the range of frequencies or wavelengths extending from infrared to ultraviolet radiation and including visible light. The term "speculum" as used herein, shall refer to a portion of an instrument adapted for being inserted into a body passage and/or placed externally of a patient, for inspection of the patient.

Turning now to the Figures in greater detail, as shown in FIG. 1, dental/medical instrument 10 comprises a unitary body 12 including a manually engagable pistol-type grip portion 13 and a speculum portion 14. As also shown, body 12 includes an integral video display 20 as well as user actuatable controls including a power or on/off switch 22 and a focus control 24. The instrument 10 also includes integral battery recharging contacts 26 and one or more external ports 28, which will be discussed hereinbelow.

Turning now to FIG. 2, lens 30 of the image capture device 16 is disposed within the speculum 14 of the instrument 10. Moreover, in the embodiment shown, various components of the image capture device 16, including lens 30 disposed within a lens housing 32, and an image sensor 34, are preferably disposed within the speculum 14. As also shown, lens 30, housing 32 and sensor 34 are all disposed in image capturing alignment with one another to capture images disposed along an axis of examination 36. Such image capturing alignment may be provided by disposing both the lens 30 and sensor 34 along a common axis (i.e., axis 36) as shown. Alternatively, this image capturing alignment may be provided by utilizing an optic coupling such as a light pipe, fiber optic coupling or other wave guide (similar to fiber-optic coupling 46 discussed hereinbelow) to couple the lens 30 with the sensor 34. One skilled in the art will recognize that use of such an optic coupling advantageously permits the sensor 34 to be disposed at various locations within the instrument 10, either on or off the axis of examination 36. Moreover, as mentioned hereinabove, such an arrangement may also facilitate use of a remote sensor 34, such as a remote digital camera, coupled optically and/or electronically to lens 30 through a port 28. Instrument 10 also includes an internal light source 38 which includes a light generator 40 such as an array of light emitting diodes (LEDs) 42 disposed on a printed circuit board 44. Light source 38 further includes an optical coupling such as a light pipe or fiber-optic coupling 46 optically coupled to a light outlet 48. As shown, light outlet 48 preferably includes distal or terminal portions of the light pipe 46 which are splayed for disposition about the periphery of lens housing 32. As shown, each of these terminal portions extends substantially parallel to axis of examination 36 to emit light along light emission axes 37 which are substantially parallel to the examination axis 36. Depending on the application (as discussed hereinbelow with respect to FIGS. 6a-6e), such substantially parallel light emission may include light emitted along one or more light emission axes 37 oriented to extend either slightly convergently towards axis 36, or slightly divergently away from axis 36. In this regard, the instrument 310 of FIG. 6d may utilize one or more slightly convergently disposed light emission axes to illuminate a relatively small area of a patient. Conversely, instrument 210 of FIG. 6c may utilize slightly divergent light emission axes, or a combination of convergent and divergent light emission axes, to illuminate a relatively larger area of the patient (i.e., to inspect a region of a patient's skin). In this manner outlet 48 emits light nominally coaxial with axis of examination 36.

Although light generator 40 preferably includes LEDs 42 as shown, any suitable light generation means, such as miniature incandescent bulbs, compact florescent lighting, or one or more lasers may be utilized. Image sensor 34 may be any suitable miniature video image capture device known to those skilled in the art, such as, for example form factor video cameras, semiconductor chip mounted CCD devices, or other devices commonly utilized in the field of electronic or digital photography. In this regard, the image capture device 16 of the present invention provides nominally the same capabilities commonly associated with conventional digital cameras and the like, namely, the ability to digitally capture, store and retrieve images for display and/or transmission. Such image transmission may be accomplished in a known manner, such as by use of port 28.

As also shown, a focus control switch 24, such as a user actuatable thumb wheel as shown, is operatively coupled by cable 50 to the lens housing 32 to focus the image captured by image sensor 34. In one embodiment, focus control 24 may include a mechanical gear-type control which actuates a cable 50 to effect focusing movement of the lens 30 relative to sensor 34 in a known manner. In such an embodiment, cable 50 may be a conventional mechanical cable. In an alternate embodiment, cable 50 may include an electric wire which serves to couple electrical signals from focus control 24 to an electrical actuator (not shown) coupled to the lens 30 to effect the focusing movement.

Moreover, all or a portion of speculum 14 is advantageously coupled modularly, i.e., in a snap-fit type arrangement, to the body 12 to permit convenient replacement and/or substitution thereof to facilitate various discrete uses. For example, a nose portion 15 (also referred to as "lens subsystem") of the speculum 14 may be modularly engagable with the display portion 17 thereof, as will be discussed in greater detail hereinbelow with respect to FIGS. 6a-6e.

The instrument power supply includes a DC-DC converter 52 electrically coupled to a DC-AC power inverter 54. Power inverter 54 is, in turn, electrically coupled to video display 20. In a particular embodiment, as shown, instrument 10 includes an internal power source such as a rechargeable or non-rechargeable battery 56 electrically coupled to DC-DC converter 52. Video display 20 is preferably a color liquid crystal display (LCD) monitor disposed integrally within body 12 in spaced relation to lens housing 32 along, e.g., intersecting, axis of examination 36 at a proximal end thereof. An example of a suitable display 20 is a 1.8 inch (4.6 cm) high density LCD display available from Prime View International Co., Ltd., Model P18BD1. Moreover, in particular embodiments, the substantially planar screen portion 21 of display 20 is disposed substantially orthogonally to the proximal portion of axis of examination 36. Such placement of monitor 20 advantageously places a displayed image generally within a natural line of sight of speculum 14 defined by axis of examination 36. This use of the integral video display 20 advantageously provides an integrated one-piece instrument 10 which enables a user to view an image which moves in a natural and intuitive manner in response to movement of the instrument 10 by a user. Advantageously, this action facilitates proper use with little or no training to generally enable a user to operate the instrument with greater tactile sensitivity than prior devices which utilize discreet video displays located remotely from the image sensing device. The use of an integral display 20 disposed within the axis of examination 36 also advantageously tends to improve the efficiency of the examination procedure by enabling the user to look in a single direction for viewing the image captured on the monitor 20, the instrument 10 and the patient while manipulating the instrument 10. This aspect thus provides improved ergonomics to enable manipulation of the instrument 10 with greater accuracy than prior art devices which generally require the user to manipulate the device while looking away from the patient to view a remote monitor.

Turning now to FIG. 3, a rechargeable power source 56 is electrically coupled to contacts 26 which, in turn, are adapted for connection to an AC power source 58. Internal power source 56 is coupled to DC-DC converter 52 which, as shown, is coupled to a light generator 40 which is coupled to light pipe 46. DC-DC converter 52 is also coupled to the DC-AC inverter 54 to supply power to a backlight 60 of video display 20. As further shown, DC-DC converter 52 provides power to a video converter 62 which provides an electronic image signal to the display 20 as well as to external video port 28. Port 28 may be coupled a remote video display 64, either directly, or via a computer network (i.e., an intranet or the Internet. As also shown, lens 30 is optically coupled to sensor 34 which is, in turn, electronically coupled to the video converter 62. Focus control 24 is electrically and/or mechanically coupled to the lens 30.

Figure 4:
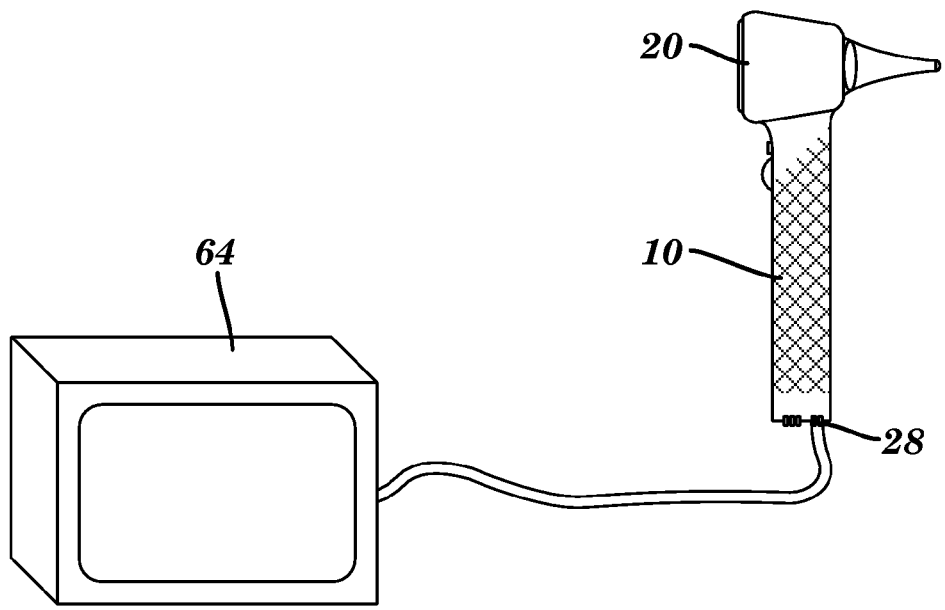
FIG. 4 is a perspective view of the instrument of FIG. 1 including an additional component of the present invention.

Turning now to FIG. 4, in a particular embodiment inspection device 10 is adapted for being coupled by its external video port 28 to a remote monitor 64. The remote monitor 64 may comprise a LCD display, television monitor, and the like, and is preferably wall mounted or movably mounted to enable a patient to view captured images in real time as the dentist or physician views the captured images on the integral display 20. This aspect of the present invention thus provides the user with a useful tool for explaining and or describing the examination process to the patient. Moreover, the image may be recorded by connecting the video output to a suitable image recorder such as a computer or VCR or other recording device.

Figure 5:
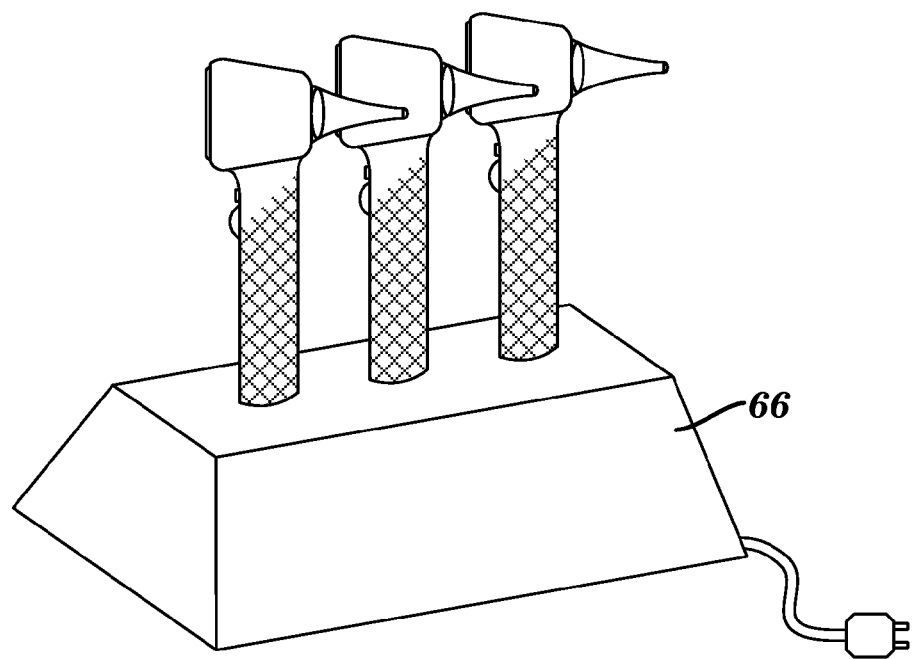
FIG. 5 is a perspective view of a plurality of instruments of FIG. 1 disposed in an optional charging device.

As shown in FIG. 5, an AC powered recharging base 66 may be utilized to receive one or more instruments 10 for recharging power source 56 by coupling external charger contacts 26 (FIG. 1) to AC power supply 58 (FIG. 3).

Turning now to FIGS. 6a-6e, in addition to the instrument 10 discussed hereinabove, various alternate embodiments of the present invention are shown as instruments 110, 210, 310 and 410. These embodiments are substantially similar to instrument 10, while utilizing various modular nose portions to facilitate discrete medical/dental examination procedures, as mentioned hereinabove. Nose portion 15 (FIG. 6a) of the speculum 14 is thus modularly engagable with the display portion 17 thereof for convenient replacement with various alternate nose portions 115, 215, 315 and 415 (FIGS. 6b-6e, respectively). In this regard, an electric focus control arrangement utilizing an electric cable 50, as discussed hereinabove with respect to FIG. 2, is preferably provided. Moreover, a light source 38 and image capture device 16 (FIG. 2) are preferably disposed entirely within each modular (removable) nose portion. These arrangements advantageously simplify modular connection between the nose portions and the display portion 17, by permitting use of conventional modular electrical connectors. Alternatively, the light source 38 may be disposed within the display portion 17, with the light pipe 46 (FIG. 2) fabricated as two discrete portions that are axially aligned with one another when a particular modular nose portion is engaged with the display portion 17.

Figure 6:
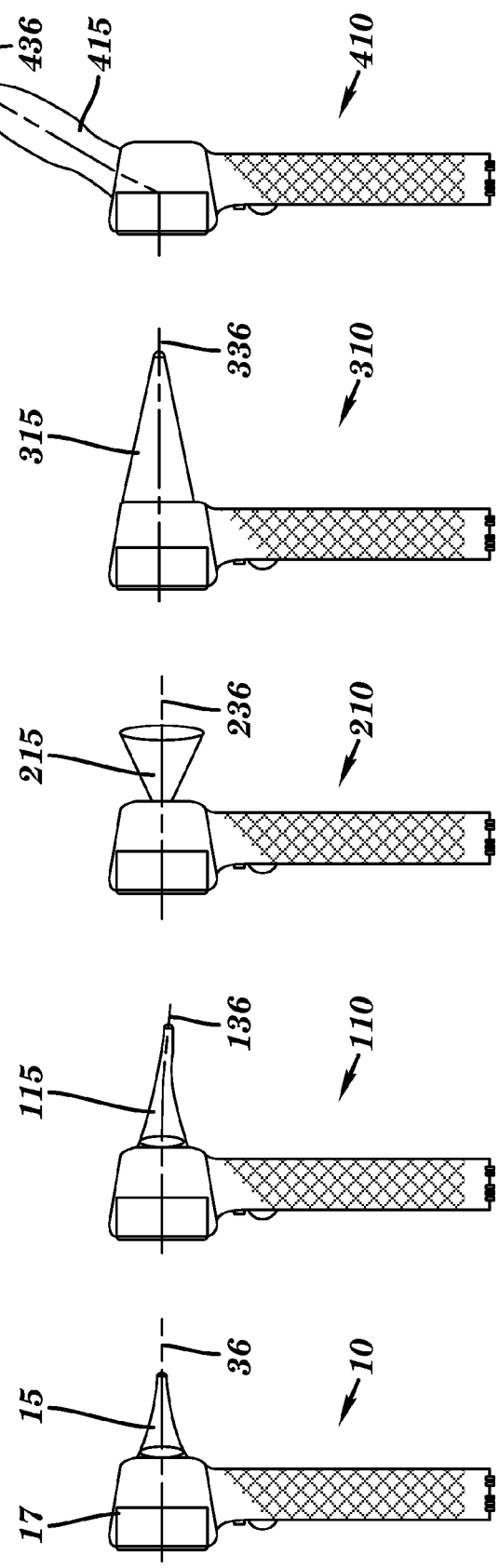
FIGS. 6a-6e are elevational views of alternate embodiments of the dental/medical inspection instrument of the present invention.

As shown, instrument 10 may be conveniently utilized to enable a physician to examine a patient's ear, nose, and throat. As shown in FIG. 6b, an extended and slightly angled nose portion 115 may be utilized to examine a patient's middle meatus, inferior meatus, superior meatus, and oropharynx. A reversed cone nose portion or lens subsystem 215 as shown in FIG. 6c, may be utilized to examine a patient's skin. An extended nose portion 315, as shown in FIG. 6d, may be utilized to examine animals such as horses, cows, and the like. As shown in FIG. 6e, an offset lens subsystem 415 may be utilized to facilitate rectal examinations and the like.

In these alternate embodiments of FIGS. 6b-6e, the substantially planar screen portion 21 of display 20 is disposed substantially orthogonally to either the respective axis of examination 136, 236, 336 or 436, or to a plane which includes the proximal portion of the axis of examination. As discussed above with respect to instrument 10, such placement of monitor 20 advantageously places a displayed image generally within a natural line of sight of speculum 14 defined by the axis of examination. This use of the integral video display 20 advantageously provides an integrated one-piece instrument 10 which enables a user to view an image which moves in a natural and intuitive manner in response to movement of the instrument 10 by a user.

Although various components of the present invention have been shown and described as being disposed within various nose portions 15, 115, 215, 315 and 415, it should be recognized by those skilled in the art that any arrangement of components may be included or removed from the nose portions without departing from the spirit and scope of the present invention.

Still further embodiments of the present invention include one or more optional variations described hereinbelow. For convenience, these optional variations are shown and described with respect to instrument 510 of FIGS. 7 and 8. The skilled artisan will recognize that the optional variations of instrument 510 may be incorporated into any of the aforementioned embodiments (instruments 10, 110, 210, 310, and 410), without departing from the spirit and scope of the present invention.

Figure 7:
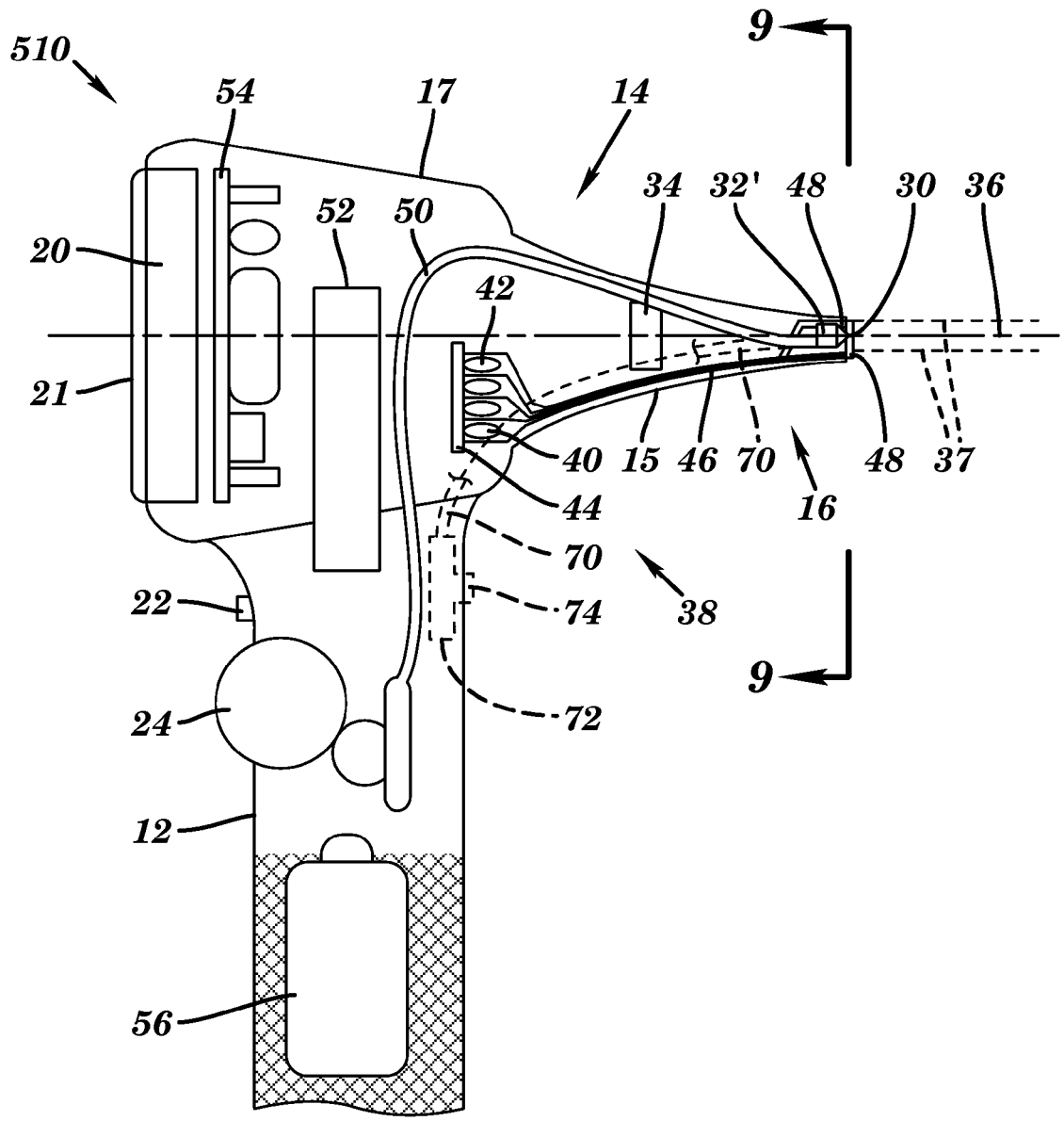
FIG. 7 is a view similar to that of FIG. 2, of an alternate embodiment of the present invention.
Figure 8:
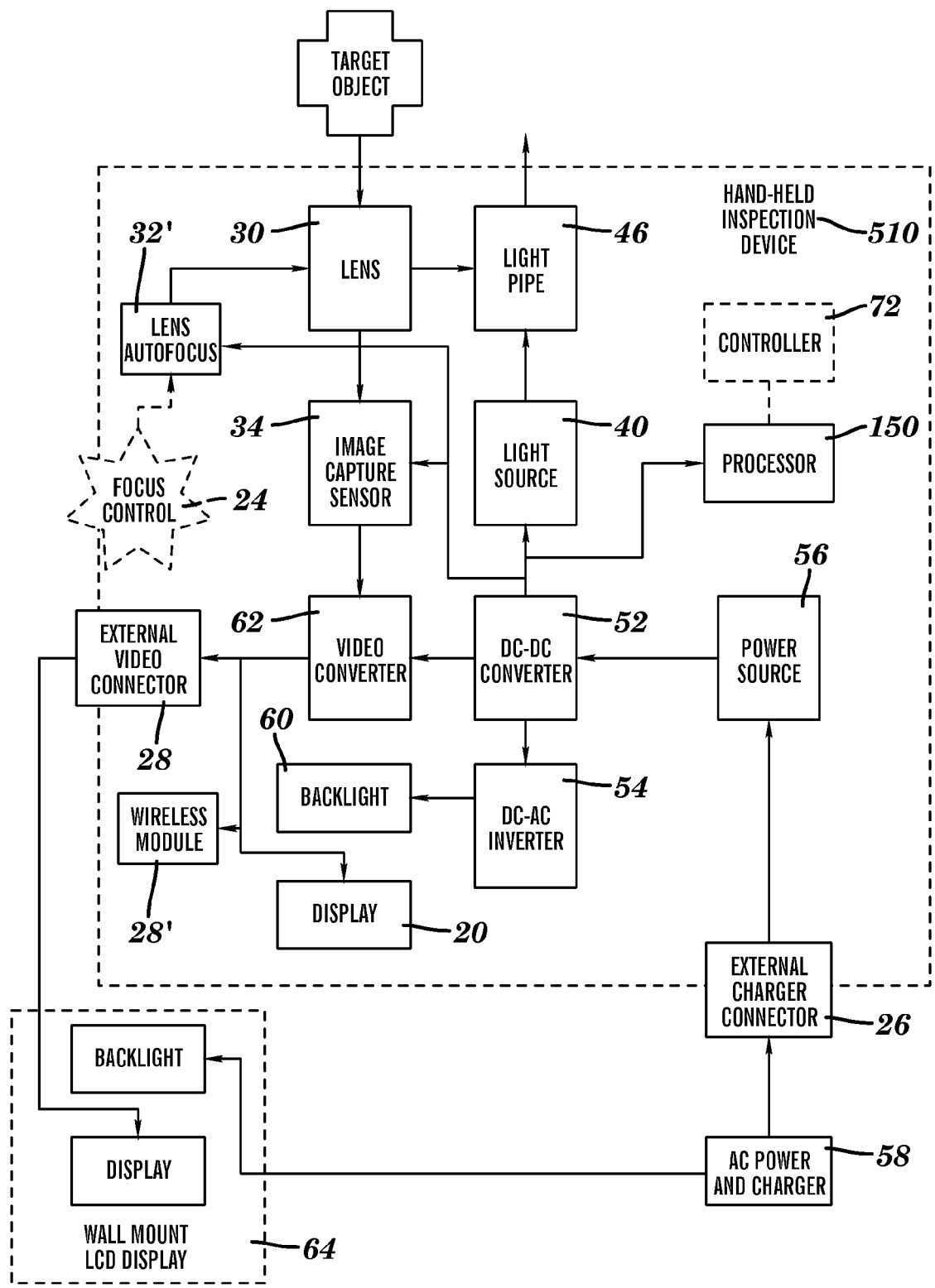
FIG. 8 is a view similar to that of FIG. 3, of an alternate embodiment of the present invention.

Turning now to FIGS. 7 and 8, instrument 510 includes various features intended to promote ease of use and/or reduce manufacturing/component cost. For example, an autofocus lens assembly including lens 30 (e.g., a fixed lens) and autofocus module 32' may be provided to substantially eliminate the need for focus control switch 24 (shown in phantom). Commercially available autofocus lens assemblies well-known in the art may be used as part or all of the autofocus lens assembly. For example, the DCV™ lens available from Edmund Scientific of Tonawanda, N.Y., USA, may be easily adapted for use in the present invention by the skilled artisan.

As a further option, the focus control 24 may be provided in addition to the autofocus lens assembly, to enable the user to manually focus the image if desired. In this embodiment, autofocus module 32' is connected to power source 56, such as by cable 50 coupled to DC-DC Converter 52 as shown.

In addition, a wireless module 28' may be used in lieu of, or in addition to, video connector 28, to enable wireless connection to video display 64' (not shown), which is similarly equipped with a wireless module 28'. Wireless module 28' may enable wireless transmission of both video and audio information as described hereinbelow. Examples of suitable wireless modules include BLUETOOTH™ chips. (BLUETOOTH™ is a trademark of telefonaktienbolaget L. M. Ericsson, Sweden.)

Instrument 510 may further include a voice recognition module 150 coupled to converter 52 as shown. This module 150 may include a microprocessor programmed with speech recognition software, such as Dragon Naturally Speaking™ voice recognition software available from L & H Dragon Systems, Inc. of Newton, Mass., USA. Voice recognition module 150 may be used to recognize voice commands capable of effecting one or more of various operations of instrument 510. For example, module 150 may recognize a voice command to capture an image (i.e., take a snapshot). Module 150 may also recognize a command to record audio information associated with a particular snapshot. For example, an examining physician may use this functionality to record a brief audio description of a particular captured image. This audio information may then be wirelessly transmitted by module 28', along the associated image, to a display 64, or to any other desired destination, such as a computer, server, or network such as the Internet.

Although several alternate configurations of nose portions or lens subsystems have been provided, those skilled in the art should recognize that nose portions or lens subsystems of substantially any geometry or construction may be utilized without departing from the spirit and scope of the present invention.

Figure 9:
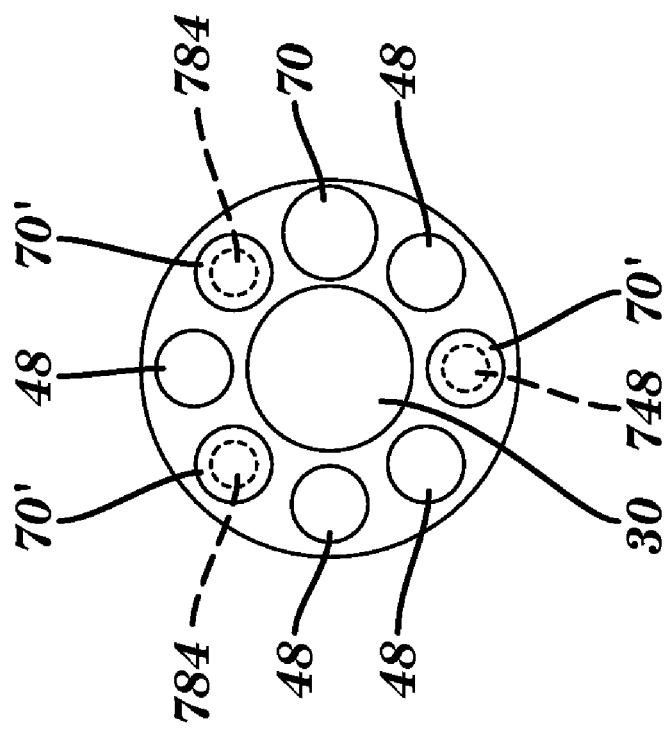
FIG. 9 is a cross-sectional view, with optional features shown in phantom, taken along 9-9 of FIG. 7.

A still further optional variation is also shown and described with respect to instrument 510 of FIGS. 7 and 8, and with respect to FIG. 9. The skilled artisan will recognize that the optional variations of instrument 510 may be incorporated into any of the aforementioned embodiments (instruments 10, 110, 210, 310, and 410), without departing from the spirit and scope of the present invention.

Turning now to FIG. 7, instrument 510 may be further equipped with a channel (e.g., tube) 70 having a proximal end coupled to a controller 72, and which extends to a distal end disposed at the distal end of speculum 16. Channel 70 advantageously provides a user with a discrete pathway for communicating with the specific area being viewed. For example, controller 72 may include a compressed air supply, to enable channel 70 to feed air to the area of the patient being viewed. Similarly, controller 72 may include a medicine supply, to enable a user to supply medicine or other treatment through channel 70 to nominally the precise point being viewed. As a still further alternative, a sensor, such as a thermocouple or other transducer, may be disposed within channel 70, to capture information at the location being viewed. In this latter example, the sensor may be coupled to controller 72, which in turn, may be configured to transmit the captured (e.g., temperature) data to processor 150 (FIG. 8) for output on display 20, 64, or 64', etc.

Controller 72 may be voice actuated, such as described hereinabove. Alternatively, controller 72 may include a trigger-type or similar actuator 74 configured for engagement by a user's finger.

Figure 10:
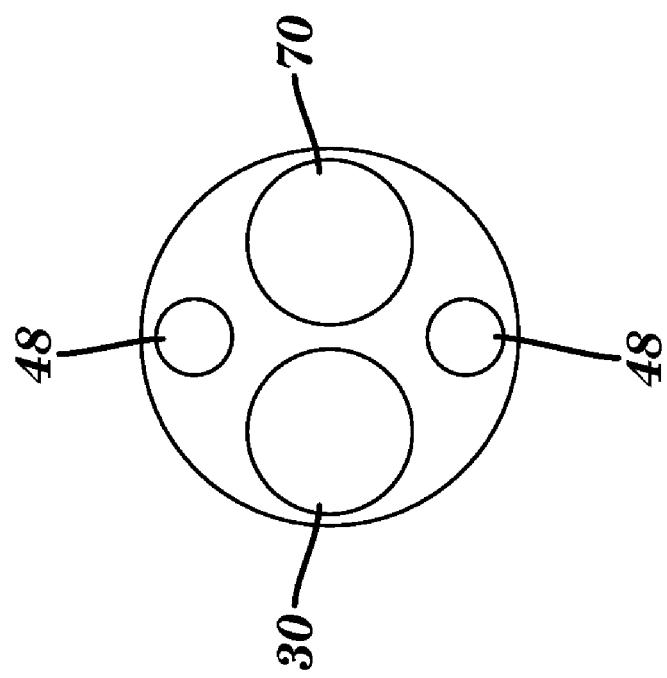
FIG. 10 is a view similar to that of FIG. 9, of an alternate embodiment of the present invention.

Exemplary configurations of the distal end of speculum 16 are shown in FIGS. 9 and 10. As shown in FIG. 9, the distal end of channel 70 may be interspersed among the splayed ends of light pipe 46 forming light outlet(s) 48. In the configuration of FIG. 10, channel 70' is enlarged relative to channel 70, such as to accommodate the flow of relatively viscous fluids (e.g., medicines) therethrough. The number of light outlets 48 may be reduced as shown, to provide clearance in the speculum tip for the channel 70'.

Exemplary use of inspection device 510 is described in connection with Table 1 below.

TABLE 1

| | |
|---|---|
| 80 | Remove inspection device from charging cradle |
| 82 | Activate power switch to actuate device |
| 84 | Optionally receive Patient ID |
| 86 | Optionally record Patient ID |
| 88 | Optionally record additional patient info, e.g., name, purpose of visit, symptoms, insurance information, etc. |
| 90 | Capture and display visual information (e.g., image(s)/video) |
| 92 | Optionally record the visual information of 90 |
| 94 | Optionally capture and record audio information (e.g., diagnoses/comments) |
| 96 | Optionally actuate channel 70 and controller 72 to: capture patient data such as temperature; supply fluid (e.g., air or medicine) to the patient; and/or effect movement of the distal end of the tip |
| 98 | Optionally record actuation of 96 |
| 100 | Optionally associate recorded information of 88, 92, 94, and/or 98 with Patient ID |
| 102 | Optionally associate recorded information of 88, 92, 94, and/or 98 with time/date |
| 104 | Optionally transmit recorded information via port 28/module 28' |
| 106 | Deactivate device |
| 108 | Place device in cradle for charging |

As shown, a user initially disconnects or removes 80 the inspection device 510, etc., from a charger, e.g., from a charging cradle. The user may activate 82 the device in any convenient manner, such as by use actuating switch 22 or by voice activation. In particular embodiments, the device receives 84 and records 86 a user-supplied Patient ID, by voice-recording or other suitable input means familiar to those skilled in the art. These embodiments further permit a user to record 88 additional patient information, such as patient name, purpose of visit, symptoms, and insurance information, etc. The user may then capture and display 90 visual information, some of which may be selectively recorded 92 as video segments and/or still images. These embodiments may also enable a user to capture and record 94 audio information such as diagnoses or other user comments.

The user may further enable a user to actuate 96 the controller 72 and channel 70. As discussed above, actuation 96 may be effected by operation of switch 74, by voice-activation, Radio Frequency (RF) or Infra-Red (IR) control, or any other conventional means known to those skilled in the art. In the event channel 70 is used as a transport mechanism, such actuation may supply material such as air or medicine to the patient as also discussed above. Alternatively, such actuation may serve to capture additional information, e.g., temperature or other sensor information as also discussed hereinabove. The actuation may also be recorded 98, and, along with the other recorded information, associated 100 with the Patient ID, and/or associated 102 with the appropriate time and date. The recorded information may then be transmitted 104 via port 28 or module 28' (e.g., a wireless Internet link such as a Wi-Fi or Bluetooth module). The device may then be deactivated 106 and recharged, such as by placing 108 the device in a charging cradle.

Figure 11C:
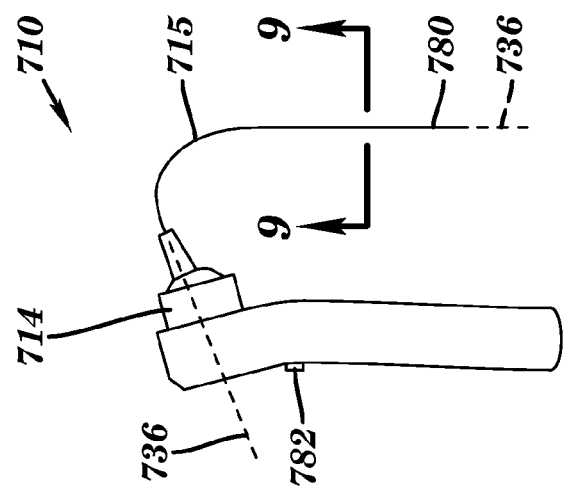
FIGS. 11A-11C are elevational views of still further embodiments of the present invention.
Figure 11B:
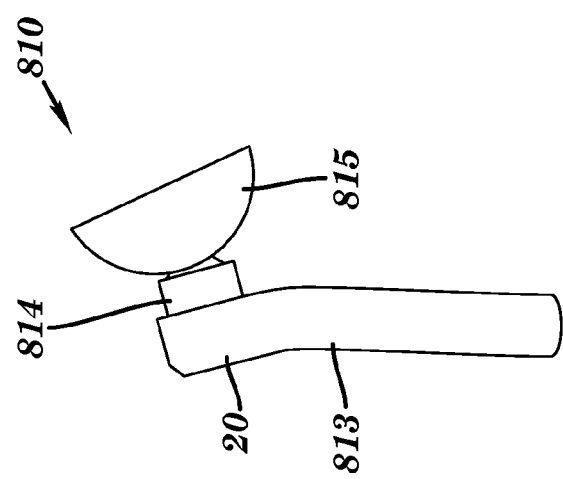
Figure 11A:
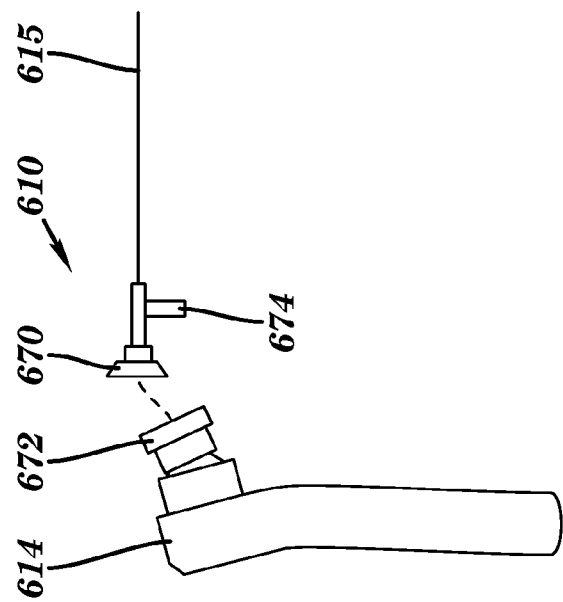

Turning now to FIG. 11, additional embodiments of the present invention, shown as 610, 710, and 810, may include characteristics of any of the foregoing embodiments, and may be configured as a fixed endoscope, flexible endoscope, or eyescope, respectively.

As shown, scope 610 includes a detachable nose portion 615 configured as a conventional endoscope. Nose portion 615 is connected to speculum portion 614 in any convenient manner, such as using mutually engaging twist-lock couplers 670 and 672 as shown. Couplers 670 and 672 may include a conventional Endoscope Video Adapter, such as available from Lighthouse Imaging Corporation of Portland, Me. Nose portion 615 may also include a conventional optical input 674 such as commonly used to connect to an external light pipe (not shown) for illumination, to facilitate image capture.

Scope 710 includes a flexible nose portion 715, with an integral actuator configured to enable a user to conveniently move the tip 780 (and the distal end of the axis of examination 736) as desired. In an exemplary configuration, the actuator is a multi-cable device, such as a miniaturized version of those commonly used in the automotive industry to actuate electric rear-view mirrors. As shown in FIG. 9, in this embodiment, a series of three or more cables 784 may be slidably disposed within flexible concentric tubes 70' interspersed among light pipes 48. Selective movement of cables 784 within tubes 70', such as effected by thumb switch/joy stick 782, serves to 'steer' tip 780 as desired. Such manueverability advantageously enables scope 780 to be used in complex procedures, such as those requiring navigation within a patient's nasal cavity or respiratory tract.

Turning now to FIG. 11B, scope 810 includes a semi-spherical cup 815 configured for nominally air-tight engagement with a patient's face over a patient's eye. An image capture assembly, (e.g., lens 30, image capture sensor 34 and light pipe 46 of FIG. 8) disposed within speculum portion 814 may be used to capture images (either still photos, or video, as discussed hereinabove) of the patient's eye/retina. The cup 815 may be fabricated from an optically transparent or transluscent material to facilitate this image capture. The sensor assembly may be provided with a manual or automatic focus adjustment, such as discussed above, to accommodate distinct focal distances as the sensor is moved, as discussed hereinbelow.

Speculum portion 814 may be slidably engaged with cup 815, so that it may be moved to various locations along the surface of the cup to capture of images of distinct portions of the patient's retina. In addition, display 20 may be mounted on a gimble mechanism (not shown) so that display 20 may be adjusted for optimal viewing by the physician, regardless of where the sensor/speculum 814 is located on cup 815. Alternatively, a mirror, prism, or other image-directing system may be used to optimize viewing from various angles to display 20.

Any suitable engagement configuration may be used to provide the slidable engagement of speculum 814 with cup 815. For example, a magnetic mount may be used to sandwich the cup 815 between speculum 814 and a ferromagnetic ring disposed on the concave side of cup 815. Such an arrangement may permit the portion 814 and ring to be moved as a unit, to substantially any portion of the cup. Another approach may be extend a plurality of tracks along the convex surface of cup 815. Speculum portion 814 may then be provided with a geometry configured for capture within those tracks, to enable portion 814 to move along the tracks as desired.

Moreover, eyescope 810 may include a frame having a nose-engagement portion (not shown), e.g., configured to engage the bridge of a patient's nose, to properly position the cup 815 over the patient's eye. Use of the nose-engagement portion enables the eyescope 810 to be conveniently rotated 180 degrees for examination of the patient's other eye.

Optionally, light generator 40 may include LEDs 42 (FIG. 8) of various colors, which may be selectively actuated, using any suitable switching means, including the aforementioned voice actuation, to test the patient's color sensitivity.

Still further, provision may be made for momentarily pressurizing cup 815 (e.g., using controller 72 configured as a compressed air supply, and channel 70, as discussed hereinabove), to facilitate conventional glaucoma testing.

Thus in use, eyescope 810 enables a user to simply rotate the handheld portion 813 and 814 around the patient's eyeball to capture images from various distinct angles. This advantageously enables a user to obtain relatively high quality images without the use of conventional (and relatively expensive) lens systems capable of relatively narrow fields of view. Also, because of precision and speed (e.g., sub-second) with which images may be captured, this embodiment may also be used to capture high quality retinal images without the need to use medicine to dilate the patient's iris. This characteristic may represent a significant improvement or breakthrough relative to the prior art.

Figure 12:
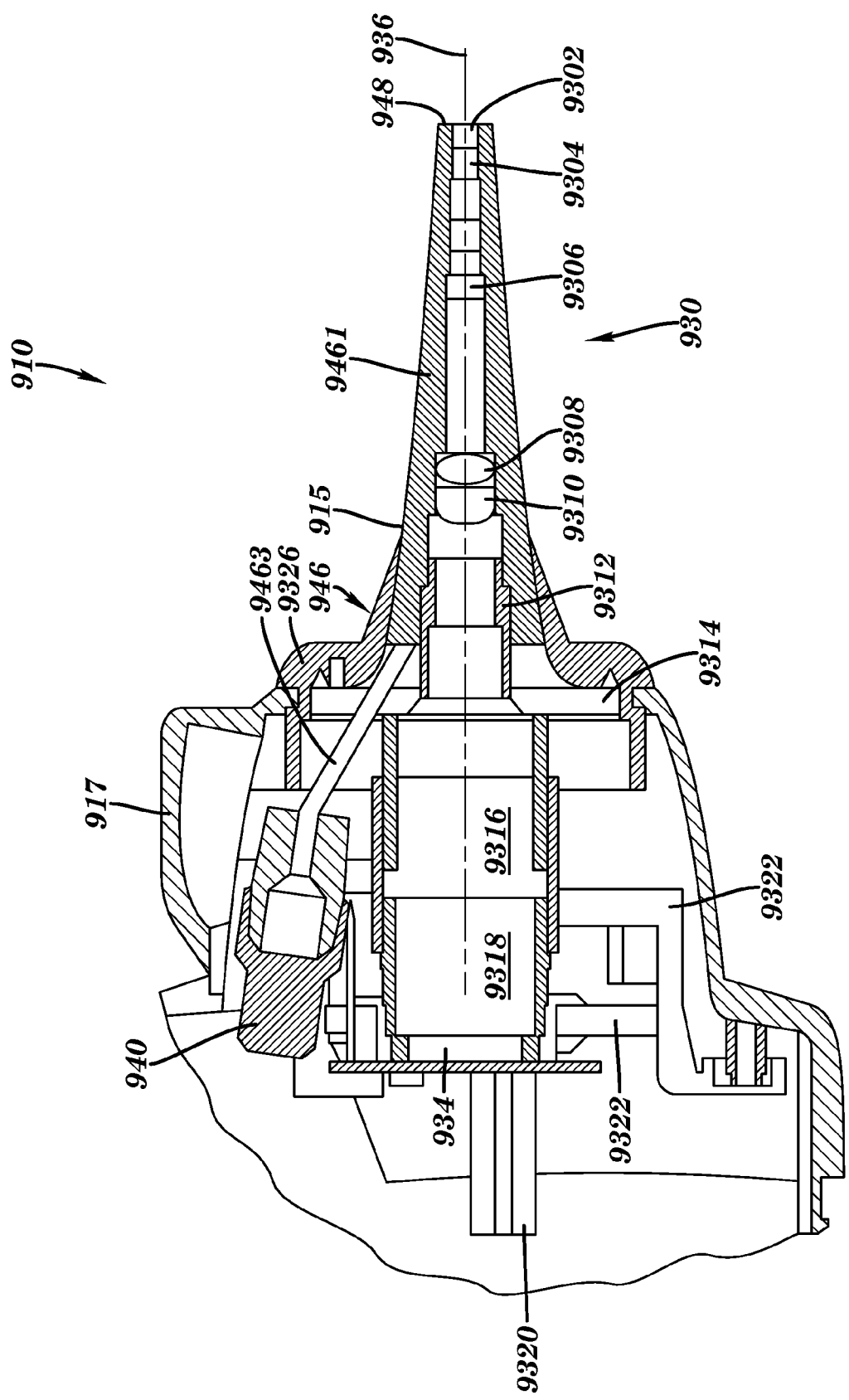
FIG. 12 is a view similar to that of FIG. 2, of a portion of an alternate embodiment of the present invention.
Figure 13:
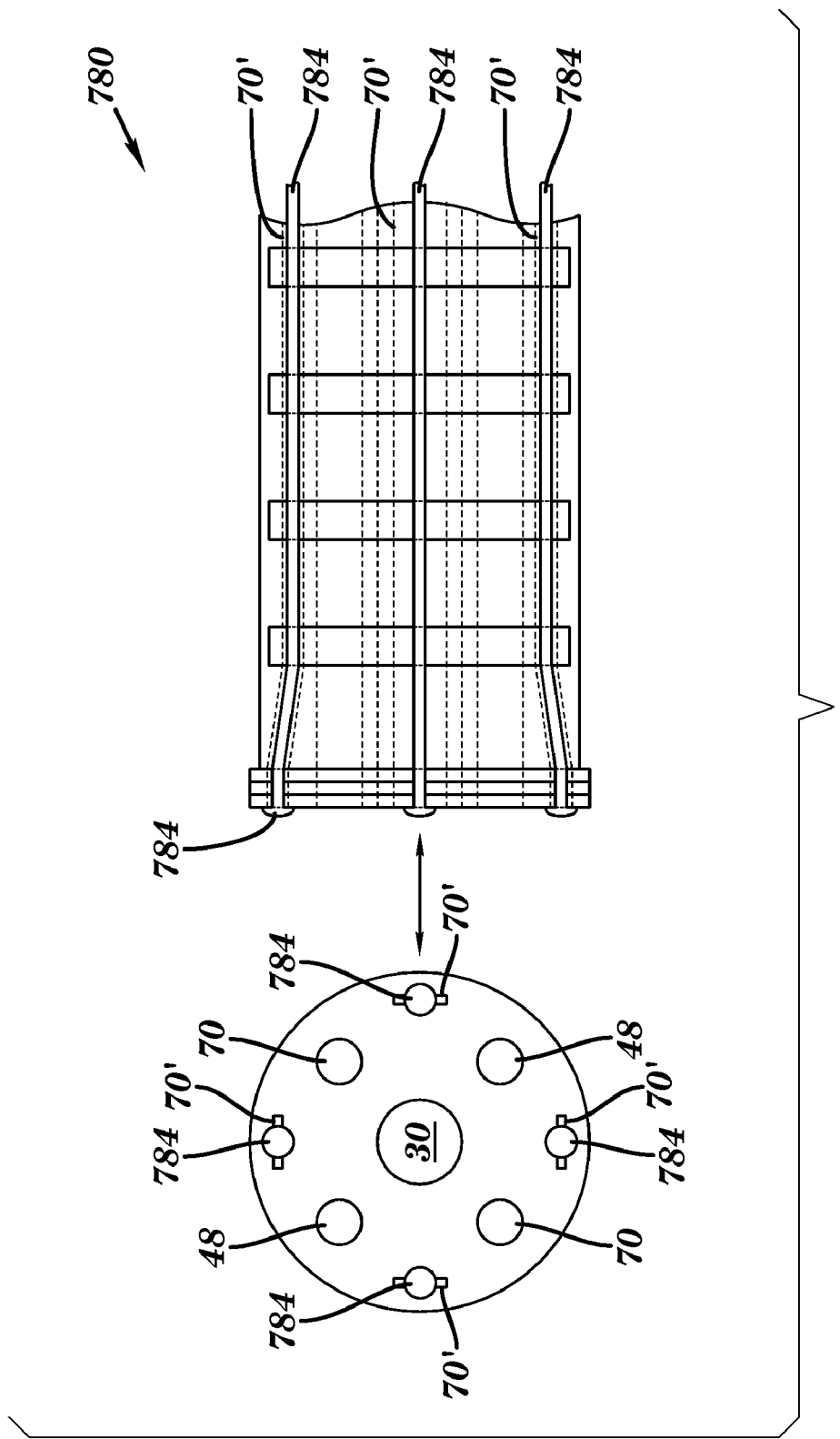
FIG. 13 is a side elevational view on an enlarged scale of a tip of a nose portion of an embodiment of the present invention, with portions broken away and portions shown in phantom.

Turning now to FIG. 12, a particular embodiment of autofocus module 32 is shown and described as module 32'. For convenience, autofocus module 32' is shown and described as incorporated within an instrument 910 having a substantially frusto-conical speculum and/or nose portion. However, those skilled in the art should recognize that module 32' may be incorporated into any of the embodiments discussed herein.

As shown, nose portion 915 of instrument 910 is provided with a fixed lens array 930 which includes a filter 9302, object lens 9304, and relay lenses 9306, 9308 and 9310, all disposed within a lens barrel 9312. Nose portion 915 also includes a light pipe portion 9461 which extends axially thereon. The nose portion 915 may be coupled to lens portion (head) 917 of instrument 910 by snap-fitting or otherwise fastening lens barrel 9312 to barrel mount 9314. While flange 9326 of nose portion 915 may be formed integrally with the housing of head 917, alternatively, nose portion 915 may be fabricated as a discrete component and secured to head 917, e.g., using fasteners to couple flange 9326 to frame 9314. This approach may facilitate the use of multiple, interchangeable nose portions, such as described herein. Barrel mount 9314 is coupled via connector 9316 to sensor barrel 9318.

As shown, lens array 930 is disposed on axis of examination 936. Image sensor 934 is supported in image capturing alignment (e.g., on axis 936) by moving guide 9320. Guide 9320 is configured to selectively move sensor 934 bi-directionally along axis 936, e.g., upon actuation of an autofocus motor 9322.

Although axis 936 is shown as being substantially straight, it may be bent or otherwise configured by the use of suitable optics, e.g., mirrors, fiber optics, or other light guides familiar to those skilled in the art, without departing from the spirit and scope of the present invention. Moreover, although sensor 934 is described as being bi-directional, i.e., being capable of movement in opposite directions along axis 936, the skilled artisan should recognize that the sensor may also be configured to move transversely to axis 936, i.e., to center and/or stabilize an image. Motor 9322 is mounted on a motor seat 9322 within the head 917.

Other components shown in FIG. 12 include light source 940 and light pipe 946, which extends from the light source to light outlet 948. These components collectively serve to illuminate a target area of a patient in the manner discussed above with respect to light source 40, light pipe 46 and light outlet 48. Moreover, light pipe 946 may extend continuously from source 940 to outlet 948, or alternatively, may extend discontinuously, such as in discrete axially aligned segments. For example, a discontinuity in the light pipe may be disposed at or proximate the frame 9314 as shown, to permit nose portion 915 to be removed from head 917 and replaced with other modular nose portions in the manner discussed above. In this manner, each such modular nose portion may be provided with a light pipe portion 9461 disposed to receive light from a light pipe portion 9463 disposed in head 917 once the nose 915 and head 917 are mutually engaged.

In operation, the fixed lens array 930, including lenses 9302, 9304, 9308 and 9310, serve to transfer an image to sensor 934. The sensor may be moved, e.g., by operation of motor 9322, to vary the depth of view of instrument 910 to focus the image. The skilled artisan will recognize that the extent of the range of depths of view obtainable by the instrument is based on the particular optics of the individual lenses, and the available travel distance of sensor 934.

Advantageously, use of the fixed lens array 930 enables the use of nose portions 915, 115, 415, etc., that have relatively low aspect ratios (ratios of width to length), to facilitate various specialized examinations in which relatively long, narrow nose portions are useful. The placement of movable lenses in the nose portion(s) may make such low aspect ratios difficult and/or prohibitively expensive to achieve.

This construction also effectively isolates any moving parts to the head 917. The nose portion(s) thus has no moving parts, which tends to reduce the complexity and cost thereof. This enables the nose portion(s) to be configured as modular, solid state components that may be quickly and easily replaced, as discussed above. Moreover, these nose portions may even be fabricated at sufficiently low cost to enable them to be discarded or recycled after a single use. Such single use devices may be used in relatively invasive procedures, to nominally prevent infections from being transmitted between patients via the instrument.

The foregoing description is intended primarily for purposes of illustration. Although the invention has been shown and described with respect to an exemplary embodiment thereof, it should be understood by those skilled in the art that the foregoing and various other changes, omissions, and additions in the form and detail thereof may be made therein without departing from the spirit and scope of the invention.

Having thus described the invention, what is claimed is:

1. A portable unitary hand-held instrument of the type selected from the group consisting of otoscopes, ophthalmoscopes, larynx scopes, nasopharynx scopes, dermatologic scopes, anoscopes, or veterinary scopes, said instrument comprising:

a body having a pistol-grip adapted for engagement by a user's hand;

said body including a speculum disposed thereon, said speculum having a proximal end and a distal end, said speculum being disposed along an axis of examination, the axis of examination extending along the length of the speculum from the proximal end to the distal end, said speculum being sized and shaped to allow location of said distal end a predetermined distance from a target;

at least one lens immovably disposed in said speculum;

at least one light outlet disposed in said speculum;

an image sensor disposed to capture a target image viewed through said lens;

an autofocus module coupled to said image sensor;

the autofocus module configured to move the image sensor relative to the lens;

a video display housed within said body, said video display being disposed on a proximal portion of the axis of examination extending through the proximal end;

a wireless communication module disposed within said instrument;

a voice recognition module disposed within said instrument;
a controller disposed within the instrument;
a tube extending from the controller to the distal end of the speculum; and
the tube configured to communicably couple the controller to an exterior of the speculum at the distal end.

2. The dental/medical instrument of claim 1, further comprising a power supply disposed integrally with said body.

3. The dental/medical instrument of claim 1, further comprising a power supply disposed integrally within said body.

4. The dental/medical instrument of claim 3, wherein said power supply is adapted for being coupled with an external power source.

5. The dental/medical instrument of claim 4, wherein said power supply further comprises charging circuitry adapted to recharge rechargeable batteries disposed integrally with said body.

6. The dental/medical instrument of claim 5, wherein said charging circuitry further comprises contacts disposed externally on said body, said contacts adapted for power coupling contact with an external power source when said body is received within a charger.

7. The dental/medical instrument of claim 1, further comprising video circuitry adapted to couple said image capture device with said video display.

8. The dental/medical instrument of claim 7, wherein said video circuitry further comprises an external port disposed on said body, said external port adapted to couple with an external video display.

9. The dental/medical instrument of claim 8, further comprising an external video display.

10. The dental/medical instrument of claim 1, wherein said video display further comprises a substantially planar screen portion, said screen portion being disposed substantially orthogonally to a plane which includes said axis of examination.

11. The dental/medical instrument of claim 1, further comprising an image recorder.

12. An examination system comprising the instrument of claim 1 and a remote audio-visual display having a wireless communication module configured to receive transmissions from the instrument.

13. A method of examining a patient comprising:
(a) utilizing a portable hand-held instrument of the type selected from the group consisting of otoscopes, ophthalmoscopes, larynx scopes, nasopharynx scopes, dermatologic scopes, anoscopes, or veterinary scopes, said instrument including:
a body having a pistol-grip adapted for engagement by a user's hand, said body including a speculum disposed thereon, said speculum having a proximal end and a distal end, said speculum being disposed along an axis of examination, the axis of examination extending along the length of the speculum from the proximal end to the distal end;
at least one lens immovably disposed in said speculum;
at least one light outlet disposed in said speculum;
an image sensor disposed to capture a target image viewed through said lens;
an autofocus module coupled to said image sensor;
the autofocus module configured to move the image sensor relative to the lens; and
a substantially planar video display housed within said body, said video display being disposed on a proximal portion of the axis of examination extending through the proximal end;
a wireless communication module disposed within said instrument, configured to communicate with a remote device;
a voice recognition module disposed within said instrument, configured to operate said instrument in response to voice commands;
a controller disposed within the instrument;
a tube extending from the controller to the distal end of the speculum; and
(b) manipulating the instrument relative to a patient while the user simultaneously faces both the patient and the video display.

14. The method of claim 13, further comprising the step of:
(c) transmitting the image to a remote display.

15. The method of claim 13, further comprising the step of:
(d) recording the image on an image recorder.

16. The method of claim 13, further comprising the step of communicably coupling the controller with the exterior of the speculum at the distal end.

17. A portable hand-held instrument of the type selected from the group consisting of otoscopes, ophthalmoscopes, larynx scopes, nasopharynx scopes, dermatologic scopes, anoscopes, or veterinary scopes, said instrument comprising:
a body having a pistol-grip adapted for engagement by a user's hand; said body including a speculum disposed thereon; said speculum having a proximal end and a distal end, said speculum being disposed along an axis of examination, the axis of examination extending along the length of the speculum from the proximal end to the distal end, said speculum being sized and shaped to allow location of said distal end a predetermined distance from a target;
a fixed lens array disposed in said speculum;
said fixed lens array including a filter and a plurality of lenses disposed in spaced relation along the axis of examination;
at least one light outlet disposed integrally with said body;
an image sensor disposed in said body to capture a target image viewed through said lens;
an autofocus module coupled to said image sensor;
the autofocus module configured to move the image sensor relative to the lens, wherein the movement is confined to the body;
a video display disposed within said body, said video display being disposed on a proximal portion of the axis of examination extending through the proximal end.

18. The instrument of claim 17, comprising:
a controller disposed within the instrument;
at least one tube extending from the controller to the distal end of the speculum; and
the tube configured to communicably couple the controller to an exterior of the speculum at the distal end.

19. The instrument of claim 18, wherein the controller comprises an air supply, the air supply configured to communicate air through the tube to the target.

20. The instrument of claim 18, wherein the controller comprises a medicine supply, the medicine supply configured to communicate medicine through the tube to the target.

21. The instrument of claim 18 wherein the controller comprises a sensor portion, the sensor portion configured to capture data from the target via the tube.

22. The instrument of claim 21, wherein the sensor portion comprises a temperature sensor portion configured to capture temperature data from the target via the tube.

23. The instrument of claim 17, further comprising:

a wireless communication module disposed within said instrument, configured to communicate with a remote device; and a voice recognition module disposed within said instrument, configured to operate said instrument in response to voice commands.

24. The instrument of claim 18, wherein the speculum is flexible, and the at least one tube comprises an actuation mechanism configured to move the speculum relative to the pistol-grip.

25. The instrument of claim 24, wherein a portion of the axis of examination disposed within the speculum is configured to move with the speculum.

26. The instrument of claim 25, wherein the at least one tube comprises a plurality of tubes.

27. The instrument of claim 26, wherein the actuation mechanism comprises a plurality of cables disposed within the tubes, the cables being coupled at proximal ends thereof to the controller, and at distal ends thereof to the speculum, said cables being selectively movable axially within the tubes to move the speculum.

28. The instrument of claim 17, wherein said lens array and said at least one light outlet are disposed integrally within a nose portion of said speculum.

29. The instrument of claim 28, wherein said nose portion further comprises a modular unit adapted for alternate engagement and disengagement with said body.

30. The instrument of claim 29, further comprising a plurality of nose portions being interchangeably engagable with said body.

31. The instrument of claim 30, wherein each of said plurality of nose portions are sized and shaped to facilitate discrete examining procedures.

32. The instrument of claim 18, comprising:

a semi-spherical cup slidably coupled to the speculum;

the cup configured for substantially air-tight engagement with a patient's face in superposed orientation with a patient's eye;

the cup fabricated from an optically transluscent material to permit capture of images of a patient's eye; and the controller including an air supply configured to communicate air through the tube to the patient's eye.

33. A portable hand-held eyescope comprising:

a body having a pistol-grip adapted for engagement by a user's hand;

said body including a speculum disposed thereon;

said speculum having a distal end disposed along an axis of examination;

a fixed lens disposed in said speculum;

at least one light outlet disposed integrally with said body;

an image sensor disposed in said body to capture a target image viewed through said lens;

an autofocus module coupled to said image sensor;

the autofocus module configured to move the image sensor relative to the lens, wherein the movement is confined to the body;

a video display disposed within said body, said video display being disposed on said axis of examination;

a controller disposed within the instrument;

a semi-spherical cup slidably coupled to the speculum;

the cup configured for superposed orientation with a patient's eye;

the cup fabricated from an optically transluscent material;

the speculum being slidable among various locations along the surface of the cup;

wherein images of the patient's eye may be captured from a plurality of angles thereto.

* * * * *